United States Patent [19]

Hermentin et al.

[11] Patent Number: 4,914,191
[45] Date of Patent: Apr. 3, 1990

[54] ANTHRACYCLINE DERIVATIVES HAVING CYTOSTATIC ACTIVITY

[75] Inventors: Peter Hermentin, Marburg; Michael Paal, Hamburg; Cenek Kolar; Hans P. Kraemer, both of Marburg; Dieter Hoffmann, Lahntal; Hans G. Berscheid, Schwalbach; Dirk Böttger, Liederbach, all of Fed. Rep. of Germany

[73] Assignee: Behringwerke Aktiengesellschaft, Marburg, Fed. Rep. of Germany

[21] Appl. No.: 216,199

[22] Filed: Jul. 7, 1988

[30] Foreign Application Priority Data

Jul. 9, 1987 [DE] Fed. Rep. of Germany ....... 3722698

[51] Int. Cl.$^4$ ...................... C07H 15/24; C07G 37/00
[52] U.S. Cl. ......................................... 536/6.4; 536/53
[58] Field of Search .................................. 536/6.4, 53

[56] References Cited

U.S. PATENT DOCUMENTS 4,039,663 8/1977 Arcamone et al. .................... 536/53
4,325,946 4/1982 Bargiotti et al. ..................... 536/6.4
4,591,637 5/1986 Acton et al. .......................... 536/6.4

FOREIGN PATENT DOCUMENTS

131942A1 12/1956 European Pat. Off. ............. 536/6.4

OTHER PUBLICATIONS

Brockmann et al., Tetrahedron Letters, No. 6, 1969, pp. 415–419, (and English language translation).
Ihn et al., The Journal of Antibiotics, vol. XXXIII, No. 12, 1980, pp. 1457–1461.
Fleck et al., Studia Biophisica, vol. 104, Nos. 1–3, 1984, pp. 215–218.

Primary Examiner—Ronald W. Griffin
Assistant Examiner—Pamela S. Webber
Attorney, Agent, or Firm—Finnegan, Henderson, Farabow, Garrett and Dunner

[57] ABSTRACT

The invention relates to new anthracycline derivatives having cytostatic activity and the general formula I

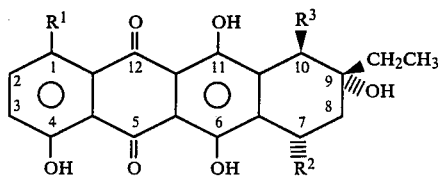

in which the radicals $R^1$ is hydrogen or a hydroxyl group, $R^2$ is hydrogen or a hydroxyl group or a structure of the formula II, and $R^3$ is a hydroxyl group or a structure of the formula II

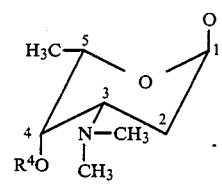

in which $R^4$ is an aliphatic or aromatic acyl group, with the proviso that at least one of the radicals $R^2$ and $R^3$ has a structure of the formula II, which are optionally in the form of a salt of an inorganic or organic acid, as well as to the process for the preparation thereof, and to the use thereof in pharmaceuticals.

13 Claims, No Drawings

ANTHRACYCLINE DERIVATIVES HAVING CYTOSTATIC ACTIVITY

The invention relates to new anthracycline derivatives having cytostatic activity and specifically relates to mono- and bis-rhodosaminyl-anthracyclinone derivatives, to a process for the preparation thereof, and to the use thereof as pharmaceuticals.

The anthracycline class of substances has been known for a long time and, since the determination of the structure of the rhodomycins, of adriamycin and of daunomycin and it became known that certain representatives of this anthracycline class have cytostatic activity, a large number of anthracyclines has been isolated by biological means from representatives of the Actinomycetes genus Streptomyces, and their activity has been investigated.

It is known that some anthracyclines such as, for example, adriamycin, daunomycin, aclacinomycin, 4'-epi-adriamycin, 4'-methoxyadriamycin or 4'-deoxyadriamycin are already used for the therapy of tumors.

A considerable problem in the use of these known anthracyclines in tumor therapy is that, besides the desired cytostatic activity, they have undesired side effects such as, for example, a hematological or cardiac toxicity.

Based on this prior art, the object of the present invention is to provide new anthracycline derivatives which show no cross-resistance and are distinguished by a new spectrum of action and lower toxicity.

This object according to the invention is achieved with new anthracycline derivatives which have cytostatic activity and correspond to the general formula I which follows

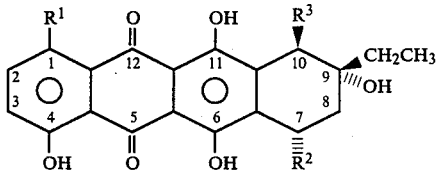

and which optionally are in the form of a salt of an inorganic or organic acid, and in which the radicals have the following meaning:

$R^1$ is hydrogen or a hydroxyl group, $R^2$ is hydrogen or a hydroxyl group or a structure of the general formula II below, $R^3$ is a hydroxyl group or a structure of the general formula II below,

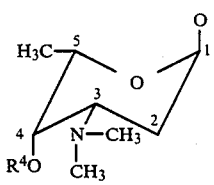

in which $R^4$ is an aliphatic or aromatic acyl group, preferably benzoyl or substituted benzoyl or an aliphatic acyl radical having 1-7 carbon atoms. At least one of the radicals $R^2$ and $R^3$ is a structure of the formula II. When both radicals $R^2$ and $R^3$ are structures of the formula II, then $R^4$ can also be hydrogen.

If $R^4$ is substituted benzoyl, then $R^4$ can be substituted in the ortho, meta and/or para position by one or more fluorine, chlorine, bromine or iodine atoms or by methoxy, nitro, cyano or azido groups. Further particularly preferred anthracycline derivatives are evident from subclaims 3 to 10 and can optionally also be in the form of acid addition salts of physiologically acceptable inorganic or organic acids.

Some anthracyclines of the formula I which contain one or two structures of the formula II with $R^4=H$ have already been known for about 2 decades (Brockmann et al., Tetrahedron Letters 1969, 415), and they can be prepared from the anthracycline compounds which are obtainable by biological means and are directly in the form of the rhodosamine derivative.

It has recently been reported that anthracyclines of the formula I in which $R^1$ is hydrogen, $R^2$ is a structure of the formula II with $R^4=H$ and $R^3=OH$ or a structure of the formula II with $R^4=H$ have antitumor activity, whereas a structure of the formula I in which $R^1=R^2=H$ and $R^3$ is a structure of the formula II with $R^4=H$ have no cytostatic activity (Fleck et al., Studia Biophysica (1984), 104, 215). Unknown as yet are compounds of the formula I which contain one or two structures of the formula II in which $R^4$ in at least one structure of the formula II is an acyl group. It has now been found, surprisingly, that compounds of the formula I which contain one or two structures of the formula II with $R^4=H$ can be selectively acylated on the 4'-hydroxyl group of this rhodosaminyl sugar segment without concomitant acylation of the other alcoholic or phenolic hydroxyl groups present in the compound of the formula I.

It has also been found that the new anthracycline derivatives of the formula I which are obtained by this and which contain one or two structures of the formula II and in which $R^1$ to $R^4$ have the said meaning have cytostatic activity without cross-reactivity with adriamycin being observed.

Based on these findings, the process according to the invention for the preparation of the new anthracycline derivatives having cytostatic activity, of the present invention, comprises reacting a compound of the formula I in which $R^4$ is hydrogen with a reactive carboxylic acid derivative, for example the corresponding acid halide, anhydride, cyanide or azide, for example of benzoic acid, a substituted benzoic acid or an aliphatic carboxylic acid, in an organic solvent such as, for example, chloroform, dichloromethane or dimethylformamide or a corresponding solvent mixture, in the presence of a base such as, for example, pyridine or triethylamine, at a temperature between, for example, $-20°$ C. and $+40°$ C., to give the corresponding 4'-O-acylated compound of the formula I.

However, a preferred process is one in which the reaction of the starting compound takes place in a two-phase system, specifically in a manner such that an organic solvent which is immiscible with water, such as, for example, chloroform or dichloromethane, is used and is stirred with an aqueous phase which contains a suitable base, for example sodium bicarbonate, it being possible to use a temperature between, for example, $0°$ C. and the boiling point of the organic solvent, which means that the reaction takes place under very mild conditions, and the reaction product accumulates in the organic phase, and allows straightforward work-up.

The reactive carboxylic acid derivative is, where the reaction is carried out in a single-phase system, expediently reacted in equivalent amount with the compound of the formula I, because in this way the formation of by-products is suppressed, and acylation takes place only on the 4'-hydroxyl group of the rhodosaminyl sugar segment.

Preferred within the scope of the invention are compounds of the formula I in which $R^4$ is benzoyl or substituted benzoyl. Likewise preferred are compounds of the formula I in which $R^1$ is H. Particularly preferred are, especially, compounds in which $R^1 = H$ and $R^4$ is benzoyl or substituted benzoyl.

The new anthracycline derivatives obtained by the process according to the invention are distinguished by cytostatic activity and can thus be processed, together with the customary pharmaceutical manufacturing aids and/or diluents, to give pharmaceuticals which are used in cancer therapy. The dosages and modes of use thereof essentially correspond to those for the known substances adriamycin, daunomycin, aclacinomycin, 4'-epi-adriamycin, 4'-methoxyadriamycin or 4'-deoxyadriamycin.

The pharmaceuticals prepared in this way can also contain further active substances as long as these do not show any undesired side effects together with the compounds according to the invention.

The cytostatic activity of the compounds according to the invention was tested using L1210 mouse leukemia cells. This made use of the formation of colonies of L1210 leukemia cells in agar plates. This method is used to detect the effect of the test substances on the growth behavior of the cells over 1 hour or over several generations. With a cell cycle lasting 10–12 hours, this means that about 14 consecutive generations are observed in a test lasting 7 days. In this test, the substances having cytostatic activity according to the invention bring about a reduction in the number of colonies to be observed by comparison with an untreated control sample.

Details of the test method are evident from the procedure for determining the formation of colonies which follows.

Procedure for determining the formation of colonies of L1210 leukemia cells in soft agar 500 leukemia cells per plate were incubated with various concentrations of the test substance at 37° C. for 1 hour. These cells were then washed twice with McCoy5A medium and finally, after addition of 0.3% agar, poured into Petri dishes. Controls were incubated only with fresh medium. In some cases, in place of the incubation for one hour, various concentrations of test substances were mixed with the upper agar layer in order in this way to achieve continuous exposure of the cells throughout the incubation time. After the agar had solidified, the plates were incubated at 37° C. in an incubator for 7 days (5% by vol. $CO_2$, 95% relative humidity). The number of colonies with a diameter of more than 60 μm which had formed was then counted. The results have been given as the number of colonies in treated agar plates as a percentage of the untreated control. The $IC_{50}$ was determined, as a measure of the activity of the substance, from the dose-effect plot obtained in this way. The results for the compounds described here, compared with adriamycin, are summarized in Table 1 which follows.

Proliferation assay (MTT reduction)

[MTT = 3-(4,5-dimethylthiazol-2-yl)-2,5-diphenyltetrazolium bromide]

L1210, A 549 or HT 29 in the exponential phase of growth are incubated in a cell density of $5 \times 10^3$ cells/ml in RPMI 1640 in a 96-well microtiter plate for 72 hours with various concentrations of the test substance at 37° C., 5% $CO_2$ and 95% relative humidity. Control experiments contain merely growth medium in place of the test substance. Each test substance and the control are determined in quadruplicate. After incubation for 65 hours, 50 μl of MTT solution (2.5 mg/ml in phosphate-buffered saline) are added. In the presence of live cells, MTT is reduced to a dark-red insoluble formazan dyestuff. This reaction is complete after 7 hours (L1210 cells) or after 24 hours (A 549, HT 29 cells), and the supernatant medium is carefully removed by aspiration. The insoluble dyestuff is dissolved by addition of 100 μl of DMSO, and the extinction of the resulting solution at a wavelength of 492 nm is then measured for each well in a Flow 340 CC multiscan photometer.

The ratio of the extinctions of treated and untreated cells yields a dose-effect plot from which the concentration which just kills 50% of the cells ($IC_{50}$) can be read off. The coefficient of variation for repeat tests is less than 15%.

Cross-resistance in vitro

The cross-resistance between the particular test compound and doxorubicin is determined using the MTT assay (for method, see above) on sensitive and resistant L1210 leukemia cells.

The resistant cell line was established by incubation of a sensitive subline with stepwise increasing concentrations of the reference compound.

The $IC_{50}$ of the test compound on the resistant subline relative to the $IC_{50}$ of the sensitive subline yields the degree of resistance both for the test compound ($DR_{(T)}$) and for the reference compound ($DR_{(R)}$) in accordance with the formula $$DR_{T,R} = \frac{IC_{50} \text{ for resistant cell line}}{IC_{50} \text{ for sensitive cell line}}$$

In addition, the degree of cross-resistance (DCR) for the test compound is calculated in accordance with the formula $$DCR \ \% = \frac{DR_{(T)} - 1}{DR_{(R)}} \times 100$$

In the case where the loss of activity of the test compound on the resistant line related to the sensitive line is greater than that of the reference compound, a degree of cross-resistance of more than 100% is possible.

The results in Table 1, part 3, show that none of the test compounds are cross-resistant to doxorubicin. The resistant cell line used is itself 60–80-fold resistant for doxorubicin.

To illustrate the preparation process according to the invention, Examples 1 to 24, in which preferred compounds according to the invention have been prepared by the claimed process, are detailed hereinafter.

The structures of the prepared compounds were established using $^1H$ and $^{13}C$ NMR and mass spectroscopy. The corresponding data are compiled in Table 2 hereinafter. The progress of the reactions and the resulting compounds were examined by thin-layer chromatography or HPLC technique.

Thin-layer chromatography was carried out on precoated silica gel plates.

Column chromatography was carried out on silica gel 60 of diameter 20–45 μm or 0.063–0.200 mm; the data on the mobile phases relate to parts by volume. The yields are not optimized.

TABLE 1

| Compounds of the formula I | | | | Adduct | Substance No. (Example) |
|---|---|---|---|---|---|
| R¹ | R² | R³ | R⁴ | | |
| Adriamycin | | | | | |
| H | II | II | Benzoyl | | 1 |
| H | II | II | Benzoyl | HCl | 2 |
| H | II | II | p-Methoxybenzoyl | | 3 |
| H | II | II | p-Methoxybenzoyl | HCl | 4 |
| H | II | II | p-Cyanobenzoyl | | 5 |
| H | II | II | p-Cyanobenzoyl | HCl | 6 |
| H | II | II | p-Nitrobenzoyl | | 7 |
| H | II | II | p-Bromobenzoyl | | 8 |
| H | II | II | Acetyl | | 9 |
| H | II | II | Propionyl | | 10 |
| H | II | II | Monobenzoyl/H | | 11 |
| H | II | II | 4′-(Mono-p-meythoxybenzoyl)/4″-H | | 12a |
| H | II | II | 4‴-(Mono-p-methoxybenzoyl)/4″-H | | 12b |
| H | II | II | Mono-p-methoxybenzoyl/H | HCl | 13 |
| H | II | II | Mono-p-cyanobenzoyl/H | | 14 |
| H | II | II | Monoacetyl/H | | 15 |
| H | II | II | Monopropionyl/H | | 16 |
| H | II | OH | Benzoyl | | 17 |
| H | II | OH | p-Methoxybenzoyl | | 18 |
| H | II | OH | p-Nitrobenzoyl | | 19 |
| H | II | OH | p-Bromobenzoyl | | 20 |
| H | II | OH | Acetyl | | 21 |
| H | H | II | Benzoyl | | 22 |

| Substance No. (Example) | Long-term incubation $IC_{50}$ (μg/ml) | 1 h Incubation $IC_{50}$ (μg/ml) | Approximative toxicity $LD_{50}$ (mg/kg) | |
|---|---|---|---|---|
| | | | 1xip | 3xip, q3d* |
| Adriamycin | 0.02 | 0.04 | | |
| 1 | — | — | >100 | |
| 2 | 0.095 | >1 | | >85 |
| 3 | 0.115 | >1 | >100 | |
| 4 | 0.09 | >1 | | |
| 5 | 0.105 | >1 | | |
| 6 | 0.14 | >1 | | |
| 7 | 2.1 | >10 | | |
| 8 | 0.3 | >10 | | |
| 9 | 0.026 | 0.06 | 3.4–6.5 | |
| 10 | 0.12 | 0.25 | | |
| 11 | 0.04 | 0.22 | 10–50 | |
| 12a | 0.0085 | 0.13 | | 10–15 |
| 12b | 0.011 | 0.1 | | 5.33–10.7 |
| 13 | 0.12 | >1 | | |
| 14 | 0.125 | 0.15 | | |
| 15 | 0.075 | 0.1 | 5–10 | |
| 16 | 0.19 | 0.25 | | |
| 17 | 0.12 | 0.9 | 1–10 | |
| 18 | 0.075 | 0.66 | 10–50 | |
| 19 | 0.03 | 0.55 | >50 | |
| 20 | — | — | | |
| 21 | 0.08 | 0.7 | 1–10 | |
| 22 | 0.48 | >1 | 1–10 | |

| Substance No. | Assay system | Incubation time | Degree of resistance of the cell | Cross-resistance to adriamycin |
|---|---|---|---|---|
| 1 | MTT | 3d | 1.0 | 0% |
| 9 | MTT | 3d | 6.0 | 6.0% |
| 12a | MTT | 3d | 0.75 | 1.3% |
| 12b | MTT | 3d | 5.0 | 5.0% |
| 13 | MTT | 3d | 2.5 | 2.5% |
| 21 | MTT | 3d | 2.2 | 2.4% |
| Adriamycin (reference) | MTT | 3d | 60–80 | 100.0% |

*3xip,q3d: three intraperitoneal administrations with an interval of three days between each
1xip: one intraperitoneal administration

EXAMPLES

Example 1

7,10-O-Bis-(4'-O-benzoyl-α-L-rhodosaminyl)-β-rhodomycinone (Compound 1)

700 mg (1 mmol) of 7,10-O-bis-(α-L-rhodosaminyl)-β-rhodomycinone ("β-rhodomycin II", Brockmann et al., Tetrahedron Letters 1969, 415; South African Pat. No. 84/5538) were dissolved in 500 ml of chloroform, and 50 ml of saturated sodium bicarbonate solution was added. The mixture was cooled to 0° C. and 310 mg (2.2 mmol) of benzoyl chloride dissolved in 50 ml of chloroform were added, and the mixture was stirred at room temperature in the dark for 16 h. The organic phase was then separated off, washed twice with water, dried with magnesium sulfate and concentrated under water pump vacuum. The resulting residue was purified by column chromatography (90 g of silica gel; eluent: toluene/ethanol=10:1).

Yield: 685 mg=0.75 mmol (75%)

Example 2

HCl adduct of compound 1

(Compound 2)

Compound 1 (20 mg, 0.02 mmol) was dissolved in 3 ml of methanol, the pH was adjusted to 1 with 20 ml of 0.1N hydrochloric acid, the methanol was removed under water pump vacuum, and the solution was freeze-dried.

Yield: 21 mg=0.02 mmol (100%)

Example 3

7,10-O-Bis-(4'-O-p-methoxybenzoyl-α-L-rhodosaminyl)-β-rhodomycinone (Compound 3)

In analogy to Example 1, 2.40 g (3.42 mmol) of β-rhodomycin II were reacted with 1.30 g (7.62 mmol) of 4-anisoyl chloride, and the product was worked up.

Yield: 2.03 g=2.1 mmol (61%)

Example 4

HCl adduct of compound 3

(Compound 4)

The preparation was carried out in analogy to Example 2.

Example 5

7,10-O-Bis-(4'-O-p-cyanobenzoyl-α-L-rhodosaminyl)-β-rhodomycinone (Compound 5)

In analogy to Example 1, 300 mg (0.43 mmol) of β-rhodomycin II were reacted with 157 mg (0.95 mmol) of 4-cyanobenzoyl chloride, and the product was worked up.

Yield: 297 mg=0.31 mmol (72%)

Example 6

HCl adduct of compound 5

(Compound 6)

The preparation was carried out in analogy to Example 2.

Example 7

7,10-O-Bis-(4'-O-p-nitrobenzoyl-α-L-rhodosaminyl)-β-rhodomycinone (Compound 7)

In analogy to Example 1, 175 mg (0.25 mmol) of β-rhodomycin II were reacted with 102 mg (0.55 mmol) of 4-nitrobenzoyl chloride, and the product was worked up.

Yield: 190 mg=0.19 mmol (76%)

Example 8

7,10-O-Bis-(4'-O-p-bromobenzoyl-α-L-rhodosaminyl)-β-rhodomycinone (Compound 8)

In analogy to Example 1, 210 mg (0.30 mmol) of β-rhodomycin II were reacted with 145 mg (0.66 mmol) of 4-bromobenzoyl chloride, and the product was worked up.

Yield: 224 mg=0.21 mmol (70%)

Example 9

7,10-O-Bis-(4'-O-acetyl-α-L-rhodosaminyl)-β-rhodomycinone (Compound 9)

In analogy to Example 1, 700 mg (1.0 mmol) of β-rhodomycin II were reacted with 175 mg (2.23 mmol) of acetyl chloride, and the product was worked up.

Yield: 637 mg=0.81 mmol (81%)

Example 10

7,10-O-Bis-(4'-O-propionyl-α-L-rhodosaminyl)-β-rhodomycinone (Compound 10)

In analogy to Example 1, 300 mg (0.43 mmol) of β-rhodomycin II were reacted with 90 mg (0.97 mmol) of propionyl chloride, and the product was worked up.

Yield: 276 mg=0.34 mmol (79%)

Example 11

Mixture of

7-O-(4'-O-benzoyl-α-L-rhodosaminyl)-β-rhodomycinone (Compound 11a) and

7-O-α-L-rhodosaminyl-10-O-(4"-O-benzoyl-α-L-rhodosaminyl)-β-rhodomycinone (Compound 11b)

In analogy to Example 1, 100 mg (0.14 mmol) of β-rhodomycin II were reacted with 1 equivalent (20 mg=0.14 mmol) of benzoyl chloride. After 1 h, the organic phase was worked up as described in Example 1, and the mixture of products was separated by column chromatography (20 g of silica gel; eluent: toluene/methanol 3:1). Besides the dibenzoyl derivative (isolate 1), the compounds 11a and 11b were isolated as a mixture of isomers in the ratio 11a:11b about 1:2.

Yield: 40 mg=0.05 mmol (36%) isomer mixture

Example 12

Mixture of
7-O-[(4'-O-p-methoxybenzoyl)-α-L-rhodosaminyl]-10-O-α-L-rhodosaminyl-β-rhodomycinone (Compound 12a) and 7-O-α-L-rhodosaminyl-10-O-[4″-O-(p-methoxybenzoyl)-α-L-rhodosaminyl]-β-rhodomycinone (Compound 12b)

In analogy to Example 11, 210 mg (0.30 mmol) of β-rhodomycin II were reacted with 1 equivalent (51 mg=0.3 mmol) of 4-anisoyl chloride, and the product was worked up. Besides the di-(p-methoxybenzoyl) derivative (isolate 1), the compounds 12a and 12b were isolated as an isomer mixture in the ratio 12a:12b about 2:3.

Yield: 117 mg=0.14 mmol (47%) isomer mixture.

The isomer mixture was fractionated into each of the pure components by column chromatography using a mobile phase composed of chloroform/methanol/acetic acid/water in the ratio 77/14/7/2 (percentages by volume). The pure isomers were extracted by shaking with chloroform and with aqueous sodium bicarbonate as the other phase.

Example 13

HCl adduct of the compounds 12a/12b isomer mixture (Compounds 13a/13b isomer mixture)

The preparation was carried out in analogy to Example 2.

Example 14

Mixture of
7-O-[4′-O-(p-cyanobenzoyl)-α-L-rhodosaminyl]-10-O-α-L-rhodosaminyl-β-rhodomycinone (Compound 14a) and 7-O-α-L-rhodosaminyl-10-O-[4″-O-(p-cyanobenzoyl)-α-L-rhodosaminyl]-β-rhodomycinone (Compound 14b)

In analogy to Example 11, 300 mg (0.43 mmol) of β-rhodomycin II were reacted with 1 equivalent (71 mg=0.43 mmol) of 4-cyanobenzoyl chloride, and the product was worked up. Besides the di-(p-cyanobenzoyl) derivative (isolate 1), the compounds 14a and 14b were isolated as an isomer mixture in the ratio 14a:14b about 1:2.

Yield: 161 mg=0.19 mmol (44%) isomer mixture

Example 15

Mixture of
7-O-(4′-O-acetyl-α-L-rhodosaminyl)-10-O-α-L-rhodosaminyl-β-rhodomycinone (Compound 15a) and 7-O-α-L-rhodosaminyl-10-O-(4″-O-acetyl-α-L-rhodosaminyl)-β-rhodomycinone (Compound 15b)

In analogy to Example 11, 100 mg (0.14 mmol) of β-rhodomycin II were reacted with 1 equivalent (11 mg=0.14 mmol) of acetyl chloride, and the product was worked up. Besides the diacetyl derivative (isolate 1), the compounds 15a and 15b were isolated as an isomer mixture in the ratio 15a:15b about 1:6.

Yield: 40 mg=0.054 mmol (39%) isomer mixture

Example 16

Mixture of
7-O-(4′-O-propionyl-α-L-rhodosaminyl)-10-O-α-L-rhodosaminyl-β-rhodomycinone (Compound 16a) and 7-O-α-L-rhodosaminyl-10-O-(4″-O-propionyl-α-L-rhodosaminyl)-β-rhodomycinone (Compound 16b)

In analogy to Example 11, 100 mg (0.14 mmol) of β-rhodomycin II were reacted with 1 equivalent (13 mg=0.14 mmol) of propionyl chloride, and the product was worked up. Besides the dipropionyl derivative (isolate 1), the compounds 16a and 16b were isolated as an isomer mixture in the ratio 16a:16b about 1:4.

Yield: 38 mg=0.05 mmol (38%) isomer mixture

Example 17

7-O-(4′-O-benzoyl-α-L-rhodosaminyl)-β-rhodomycinone (Compound 17)

544 mg (1 mmol) of 7-O-(α-L-rhodosaminyl)-β-rhodomycinone ("β-rhodomycin I", Brockmann et al., Tetrahedron Letters 1969, 415) were dissolved in a solvent mixture composed of 95 ml of dichloromethane and 5 ml of pyridine. 131 mg (1 mmol) of benzoyl cyanide were added to the solution which had been cooled to 0° C. After the mixture had been stirred at room temperature for 12 h it was concentrated in vacuo, and the residue was purified by chromatography on 100 g of silica gel (eluent: toluene/ethanol 10:1).

Yield: 520 mg=0.80 mmol (80%)

Example 18

7-O-(4′-O-p-Methoxybenzoyl-α-L-rhodosaminyl)-β-rhodomycinone (Compound 18)

300 mg (0.55 mmol) of β-rhodomycin I were dissolved in 30 ml of dichloromethane/pyridine 10:1. 106 mg (0.62 mmol) of p-methoxybenzoyl chloride dissolved in 20 ml of dichloromethane were added dropwise within 0.5 h. After 3 h, 10 ml of methanol were added to the reaction mixture, and it was then concentrated in vacuo. The resulting product was purified by chromatography on 80 g of silica gel (eluent: toluene/ethanol 10:1).

Yield: 238 mg=0.35 mmol (64%)

Example 19

7-O-(4′-O-p-Nitrobenzoyl-α-L-rhodosaminyl)-β-rhodomycinone (Compound 19)

Compound 19 was prepared starting from β-rhodomycin I and 4-nitrobenzoyl chloride as described for the preparation of Compound 18.

Example 20

7-O-(4′-O-p-Bromobenzoyl-α-L-rhodosaminyl)-β-rhodomycinone (Compound 20)

Compound 20 was prepared starting from β-rhodomycin I and 4-bromobenzoyl chloride as described for the preparation of Compound 18.

Example 21

7-O-(4′-O-Acetyl-α-L-rhodosaminyl)-β-rhodomycinone (Compound 21)

In analogy to Example 11, 544 mg (1 mmol) of β-rhodomycin I were reacted with 1 equivalent (79 mg=1 mmol) of acetyl chloride, and the product was worked up. The residue remaining after removal of the solvent was purified by column chromatography (100 g of silica gel; eluent: toluene/ethanol 10:1).

Yield: 510 mg=0.87 mmol (87%)

Example 22

10-O-(4'-O-Benzoyl-α-L-rhodosaminyl)-γ-rhodomycinone (Compound 22)

In analogy to Example 11, 264 mg (0.5 mmol) of 10-O-(α-L-rhodosaminyl)-γ-rhodomycinone ("iremycin", Ihn et al., J. Antibiotics (1980), 33, 1457) were reacted with 1 equivalent (70 mg=0.5 mmol) of benzoyl chloride, and the product was worked up. The residue remaining after removal of the solvent was purified by column chromatography (50 g of silica gel; eluent: chloroform/methanol/acetic acid/formic acid 13:1:1:0.4).

Yield: 266 mg=0.41 mmol (82%)

Example 23

Alternative preparation of compounds 15a and 15b 20 mg of β-rhodomycin II were dissolved in 15 ml of chloroform, and 20 ml of saturated sodium bicarbonate solution were added and, after addition of 1 ml of acetic anhydride, the mixture was stirred at 53° C. in the dark for 1 h. The organic phase was then separated off, evaporated to dryness, extracted with chloroform and a saturated solution of sodium bicarbonate, and the product was purified by column chromatography with toluene/methanol (3:1) as eluent.

Example 24

Alternative preparation of compound 21:

In analogy to Example 23, 20 mg of β-rhodomycin I were reacted, and the product was worked up and purified by column chromatography with toluene/ethanol (10:1) as eluent.

TABLE 2

| Proton | Compound 1 | Compound 3 | Compound 5 | Compound 7 |
|---|---|---|---|---|
| H-1 | 7.91 dd | 7.92 dd | 7.93 dd | 7.88 dd |
| H-2 | 7.72 dd | 7.73 t | 7.75t[(1)] | 7.72 t |
| H-3 | 7.32 dd | 7.33 dd | 7.35 dd | 7.31 dd |
| H-7 | 5.22 m | 5.22 m | 5.22 m | 5.19 m |
| H-10 | 5.07 s | 5.06 s | 5.07 s | 5.07 s |
| $H_3$-14 | 1.15 t | 1.14 t | 1.14 t | 1.14 t |
| H-1', 1" | 5.67 s; 5.66 s | 5.65 bs | 5.65 bs | 5.66 bs |
| H-3', 3" | 2.68 ddd; 2.55 ddd | 2.68 ddd; 2.53 ddd | 2.68 m; 2.54 m | 2.93 m; 2.76 m |
| H-4', 4" | 5.52 bs; 5.49 bs | 5.48 bs; 5.46 bs | 5.52 bs; 5.49 bs | 5.59 bs; 5.56 bs |
| H-5', 5" | 4.28 q; 4.13 q | 4.25 q; 4.11 q | 4.28 q; 4.14 q | 4.32 q; 4.17 q |
| $H_3$-6', 6" | 1.23 d; 1.8 d | 1.21 d; 1.16 d | 1.22 d; 1.18 d | 1.23 d; 1.19 d |
| $N(CH_3)_2$ | 2.21 s; 2.20 s | 2.21 s | 2.22 bs | 2.35 s |
| OH-4 | 12.13 bs | 12.16 bs | 12.12 bs | [(2)] |
| OH-6 | 12.92 bs | 12.94 bs | 12.93 bs | 12.89 bs |
| OH-11 | 13.79 bs | 13.79 bs | 13.81 bs | 13.78 bs |
| OH-9 | 3.70 s | 3.70 s | 3.61 bs | [(2)] |
| Others | | 3.87 s; 3.86 s ($OCH_3$) | | |

| Proton | Compound 8 | Compound 9 | Compound 10 |
|---|---|---|---|
| H-1 | 7.90 d | 7.87 d | 7.90 d |
| H-2 | 7.73 dd | 7.71 dd | 7.72 t |
| H-3 | 7.32 d | 7.29 d | 7.31 d |
| H-7 | 5.20 m | 5.13 m | 5.16 m |
| H-10 | 5.08 s | 5.02 s | 5.03 s |
| $H_3$-14 | 1.16 t | 1.10 t | 1.3–1.1m[(3)] |
| H-1', 1" | 5.65 bs | 5.52 bs; 5.49 bs | 5.54 bd; 5.52 bd |
| H-3', 3" | 2.65 m; 2.50 m | 2.50 m; 2.40 m | 2.6–2.3 m |
| H-4', 4" | 5.50 bs; 5.45 bs | 5.25 bs; 5.21 bs | 5.27 bs; 5.24 bs |
| H-5', 5" | 4.28 q; 4.10 q | 4.18 q; 4.02 q | 4.16 q; 4.02 q |
| $H_3$-6', 6" | 1.20 d | 1.20 d | 1.3–1.1 m[(3)] |
| $N(CH_3)_2$ | 2.20 s | 2.20 s | 2.20 s |
| OH-4 | 12.10 bs | [(2)] | 12.12 bs |
| OH-6 | 12.93 bs | [(2)] | 12.88 bs |
| OH-11 | 13.80 bs | [(2)] | 13.73 bs |
| OH-9 | 3.71 bs | 3.65 bs | 3.62 bs |

| Proton | Compound 11 a | Compound 11 b | Compound 12 a | Compound 12 b |
|---|---|---|---|---|
| H-1 | | 7.91 d | 7.91 d | 7.91 dd |
| H-2 | | 7.73 t | 7.72 t | 7.72 dd |
| H-3 | 7.33 d | 7.32 d | 7.32 dd | |
| H-7 | | 5.18 m | 5.20 m | 5.17 m |
| H-10 | | 5.06 s | 5.03 s | 5.05 s |
| $H_3$-14 | | 1.13 t | 1.13 t | 1.13 t |
| H-1' | | 5.50 bs | 5.64 bd | 5.50 bs |
| H-1" | | 5.65 bs | 5.46 bd | 5.64 bd |
| H-3' | 2.55 ddd | | 2.56 ddd | [(2)] |
| H-3" | | 2.70 ddd | [(2)] | 2.68 ddd |
| H-4' | | 3.69 bs | 5.48 bs | 3.70 bs |
| H-4" | | 5.50 bs | 3.64 bs | 5.45 bs |
| H-5' | 4.28 q | 4.06 q | 4.25 q | 4.05 q |
| H-5" | 3.92 q | 4.11 q | 3.92 q | 4.11 q |
| $H_3$-6' | [(2)] | 1.40 d | 1.21 d | 1.40 d |

TABLE 2-continued

| Proton | | | | |
|---|---|---|---|---|
| H₃-6″ | 1.36 d | 1.18 d | 1.35 d | 1.16 d |
| N(CH₃)₂ | | 2.22 s | 2.20 s | 2.22 s; 2.20 s |
| OH-4 | | 12.16 bs | 12.16 bs | 12.15 bs |
| OH-6 | | 12.90 bs | 12.90 bs | 12.89 bs |
| OH-11 | 13.73 bs | 13.80 bs | 13.72 bs | 13.79 bs |
| OH-9 | | 3.75 bs | 3.64 | 3.70 bs |
| Others | | | 3.87 s (OCH₃) | 3.85 s (OCH₃) |
| | | | 8.05(d,2H), 6.93(d,2H) | 8.03(d,2H), 6.91(d,2H) Ph |

| | Compound | | | |
|---|---|---|---|---|
| Proton | 14 A | 14 B | 15 B | 16 B |
| H-1 | | 7.92 dd | 7.91 dd | 7.91 dd |
| H-2 | | 7.73 T⁽¹⁾ | 7.72 dd | 7.72 t |
| H-3 | | 7.33 dd | 7.33 d | 7.32 dd |
| H-7 | | 5.18 m | 5.17 m | 5.16 m |
| H-10 | 5.04 s | 5.05 s | 5.03 s | 5.02 s |
| H₃-14 | | 1.13 t | 1.12 t | 1.2–1.1 m⁽³⁾ |
| H-1′ | | 5.49 bs | 5.49 bs | 5.48 bs |
| H-1″ | | 5.63 bd | 5.53 d | 5.53 d |
| H-3′ | 2.51 ddd | | 2.48 ddd | 2.51 ddd |
| H-3″ | | 2.60 ddd | | |
| H-4′ | | 3.69 bs | 3.69 bs | 3.68 bs |
| H-4″ | | 5.47 bs | 5.23 bs | 5.24 bs |
| H-5′ | 4.28 q | 4.06 q | 4.03 m | 4.03 m |
| H-5″ | 3.90 q | .414 q | 4.03 m | 4.03 m |
| H₃-6′ | 1.21 d | 1.40 d | 1.40 d | 1.39 d |
| H₃-6″ | 1.35 d | 1.17 d | 1.15 d | 1.2–1.1 m⁽³⁾ |
| N(CH₃)₂ | | 2.20 s; 2.17 s | 2.20 s; 2.19 s | 2.20 s; 2.17 s |
| OH-4 | | 12.15 bs | 12.16 bs | 12.15 bs |
| OH-6 | | 12.92 bs | 12.89 bs | 12.88 bs |
| OH-11 | (2) | 13.81 bs | 13.76 bs | 13.75 bs |
| OH-9 | | 3.72 s | 3.71 s | 3.68 bs |
| Other s | | | 2.13 s (acetyl-CH₃) | |

| | Compound | | | | | |
|---|---|---|---|---|---|---|
| Proton | 17 | 18 | 19 | 20 | 21 | 22⁽⁴⁾ |
| H-1 | 7.88 dd | 7.79 dd | 7.88 dd | 7.88 dd | 7.85 dd | (2) |
| H-2 | 7.73 t | 7.67 t | 7.75 t | 7.73 t | 7.70 t | (2) |
| H-3 | 7.32 dd | 7.25 dd | 7.25 dd | 7.30 dd | 7.28 dd | 7.30 |
| H-7 | 5.16 m | 6.67 m | 5.20 m | 5.20 m | 5.12 m | (2) |
| H-10 | 4.91 s | 4.89 s | 4.93 s | 5.08 s | 4.88 s | (2) |
| H₃-14 | 1.12 t | 1.13 t | 1.14 t | 1.13 t | 1.13 t | 1.10 t |
| H-1′ | 5.70 bs | 5.57 bs | 5.70 bs | 5.65 bs | 5.54 bs | 5.67 bs |
| H-3′ | 2.95 | 2.84 m | 2.81 m | 2.65 m | (2) | 3.00 m |
| H-4′ | 5.58 bs | 5.53 bs | 5.60 bs | 5.50 bs | 5.25 bs | 5.57 bs |
| H-5′ | 4.33 q | 4.30 q | 4.35 q | 4.28 q | 4.19 q | 4.22 q |
| H₃-6′ | 1.20 d | 1.20 d | 1.24 d | 1.20 d | 1.20 d | 1.21 d |
| andere | | 3.85 s (OCH₃) | | | 2.18 s (acetyl-CH₃) | |

⁽¹⁾Overlap with aromatic signals
⁽²⁾Not determined
⁽³⁾Overlap with propionyl-CH₃
⁽⁴⁾90 MHz spectrum

We claim:

1. An anthracycline derivative having the formula I or physiologically acceptable inorganic or organic acid salt thereof

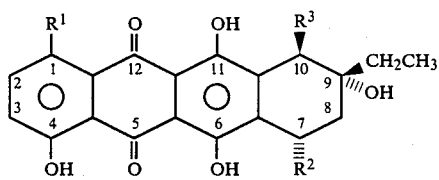

in which the radicals have the following meaning:
R¹ is hydrogen or a hydroxyl group,
R² is hydrogen or a hydroxyl group or a structure of the formula II below,
R³ is hydroxyl group or a structure of the formula II below in which R⁴ is a benzoyl, substituted benzoyl, or an aliphatic acyl radical having 1–7 carbon atoms, with the proviso that at least one of the radicals R² and R³ represent a structure of the formula II, and when radicals R² and R³ both represent a structure of the formula II, R⁴ in one of these radicals is hydrogen.

2. An anthracycline derivative as claimed in claim 1, wherein the substituted benzoyl is substituted in at least one of the ortho, meta or para position by one or more fluorine, chlorine, bromine or iodine atoms or by methoxy, nitro, cyano or azido groups.

3. An anthracycline derivative as claimed in claim 1, wherein $R^1$ is hydrogen, $R^2$ and $R^3$ each represent a structure of the formula II in which $R^4$ in both radicals $R^2$ and $R^3$ is the same having the indicated meaning group.

4. An anthracycline derivative as claimed in claim 1, wherein $R^1$ is a hydrogen and $R^2$ and $R^3$ each represent a structure of the formula II, with $R^4$ in one structure of the formula II being hydrogen and $R^4$ in the other structure of the formula II being a benzoyl, substituted benzoyl or an aliphatic acyl radical having 1–7 carbon atoms.

5. An anthracycline derivative as claimed in claim 1, wherein $R^1$ is hydrogen, $R^2$ is a structure of the formula II in which $R^4$ has the indicated meaning, and $R^3$ is a hydroxyl group.

6. An anthracycline derivative as claimed in claim 1, wherein $R^1$ is hydrogen, $R^2$ is hydrogen or a hydroxyl group, and $R^3$ is a structure of the formula II in which $R^4$ has the indicated meaning.

7. An anthracycline derivative as claimed in claim 1, wherein $R^1$ is a hydroxyl group, $R^2$ and $R^3$ each represent a structure of the formula II in which $R^4$ in both radicals $R^2$ and $R^3$ is the same having the indicated meaning group.

8. An anthracycline derivative as claimed in claim 1, wherein $R^1$ is a hydroxyl group and $R^2$ and $R^3$ each represent a structure of the formula II, with $R^4$ in one structure of the formula II being hydrogen and $R^4$ in the other structure of the formula II being a benzoyl, substituted benzoyl or an aliphatic acyl radical having 1–7 carbon atoms.

9. An anthracycline derivative as claimed in claim 1, wherein $R^1$ is a hydroxyl group, $R^2$ is a structure of the formula II in which $R^4$ has the indicated meaning, and $R^3$ represents a hydroxyl group.

10. An anthracycline derivative as claimed in claim 1, wherein $R^1$ is a hydroxyl group, $R^2$ is hydrogen or a hydroxyl group, and $R^3$ is a structure of the formula II in which $R^4$ has the indicated meaning.

11. A process for the preparation of an anthracycline derivative as claimed in claim 1, which comprises reacting a compound of the formula I in which $R^4$ is hydrogen with a reactive carboxylic acid derivative in an organic solvent or a corresponding solvent mixture, in the presence of a base, at a temperature between $-20°$ C. and $+40°$ C., to give a compound in which $R^4$ has the indicated meaning.

12. A process for the preparation of an anthracycline derivative as claimed in claim 1, which comprises reacting a compound of the formula I in which $R^4$ is hydrogen with a reactive carboxylic acid derivative in a two-phase system composed of an organic solvent which is immiscible with water and an aqueous phase which contains a suitable base.

13. The process as claimed in claim 11, wherein the compound of the formula I is reacted with an equivalent amount of the reactive carboxylic acid derivative for each sugar unit to be substituted.

* * * * *